(12) United States Patent
Dworzan

(10) Patent No.: US 7,409,741 B2
(45) Date of Patent: Aug. 12, 2008

(54) TOOTHBRUSH WITH TUNED VIBRATING HEAD

(76) Inventor: William S. Dworzan, 12351 Alexander La., Santa Ana, CA (US) 92705

(*) Notice: Subject to any disclaimer, the term of this patent is extended or adjusted under 35 U.S.C. 154(b) by 0 days.

(21) Appl. No.: 10/603,902

(22) Filed: Jun. 24, 2003

(65) Prior Publication Data
US 2004/0261203 A1 Dec. 30, 2004

(51) Int. Cl.
*A61C 17/00* (2006.01)
*A46B 13/02* (2006.01)

(52) U.S. Cl. ........................ 15/22.1; 433/122

(58) Field of Classification Search ............... 15/22.1, 15/22.2, 22.3, 22.4, 23, 28, 29; 433/122, 433/123
See application file for complete search history.

(56) References Cited

U.S. PATENT DOCUMENTS

| | | | |
|---|---|---|---|
| 3,685,080 A | 8/1972 | Hubner ..................... 15/22 |
| 5,165,131 A * | 11/1992 | Staar ....................... 15/22.1 |
| 5,189,751 A | 3/1993 | Giuliani et al. ............ 15/22.1 |
| 5,247,716 A * | 9/1993 | Bock ........................ 15/22.1 |
| 5,421,726 A | 6/1995 | Okada ...................... 433/216 |
| 5,651,157 A | 7/1997 | Hahn ....................... 15/22.1 |
| 5,706,542 A | 1/1998 | Okada ...................... 15/22.1 |
| 5,718,667 A | 2/1998 | Sugimoto et al. ........... 601/139 |
| 5,987,681 A | 11/1999 | Hahn et al. ................ 15/22.1 |
| 6,421,865 B1 * | 7/2002 | McDougall ................. 15/22.1 |
| 6,421,866 B1 | 7/2002 | McDougall ................. 15/22.1 |

* cited by examiner

*Primary Examiner*—Gary K Graham
(74) *Attorney, Agent, or Firm*—Willie Krawitz

(57) ABSTRACT

A toothbrush provides a head with bristles, a neck and a handle. An eccentrically rotational weight is engaged for rotation with a motor, the weight disposed within the head. The motor is disposed within the handle. The head and neck are integrally formed with a natural resonance frequency of vibration approximately equal to the rotational speed of the motor and synchronized therewith.

9 Claims, 5 Drawing Sheets

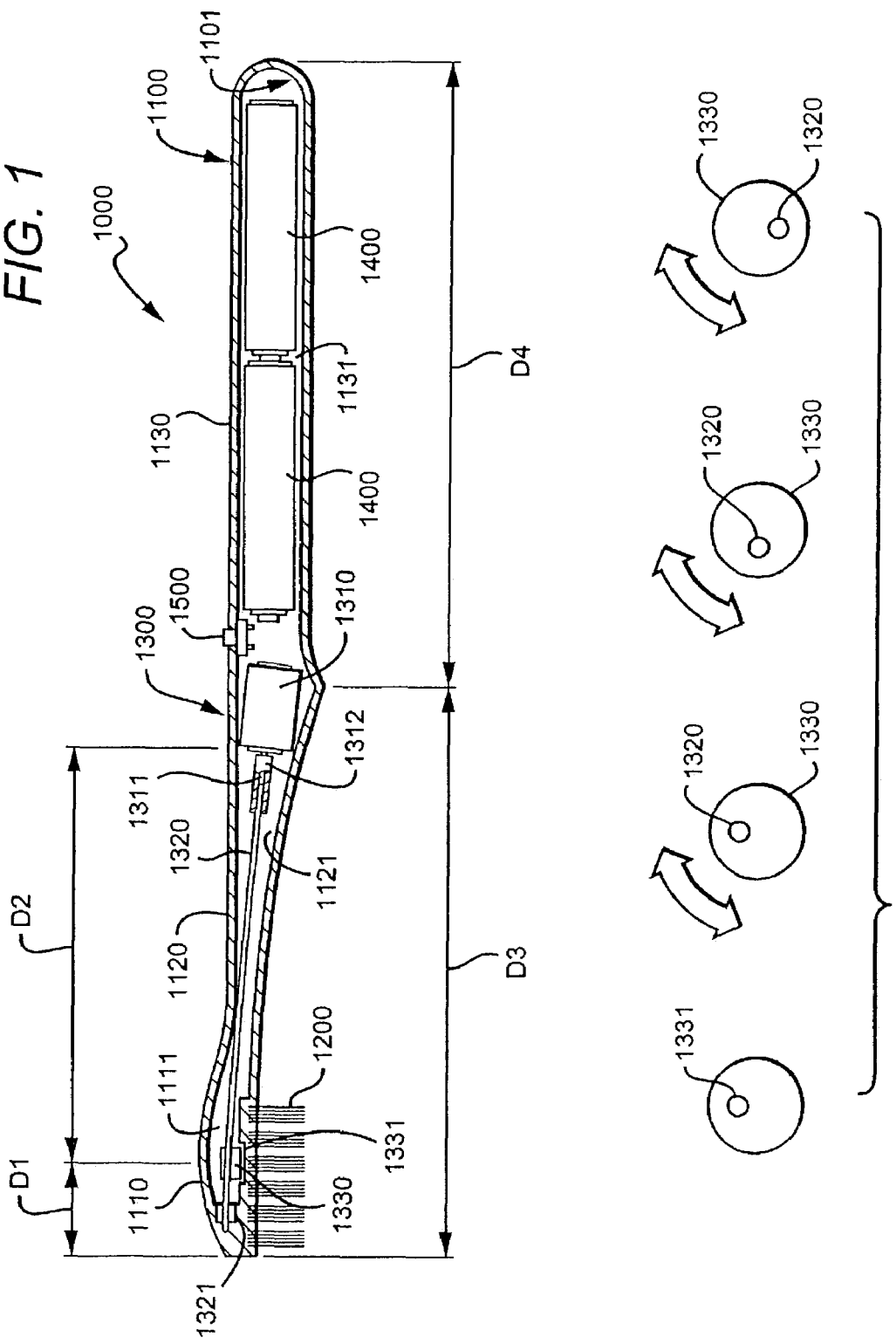

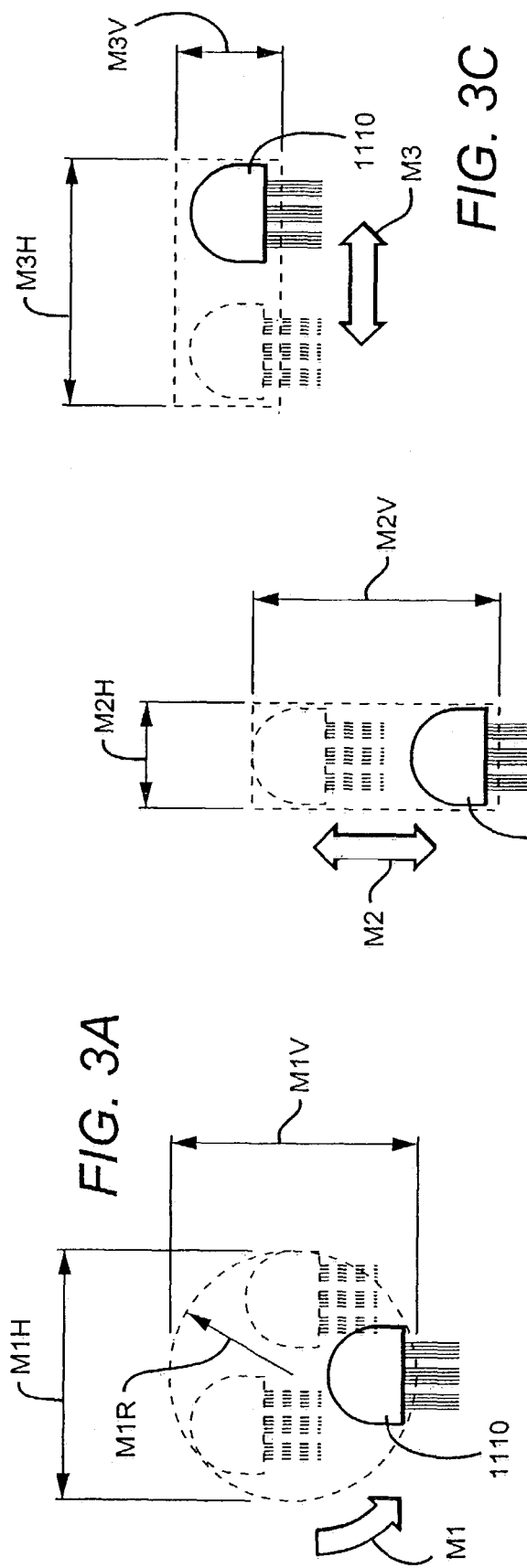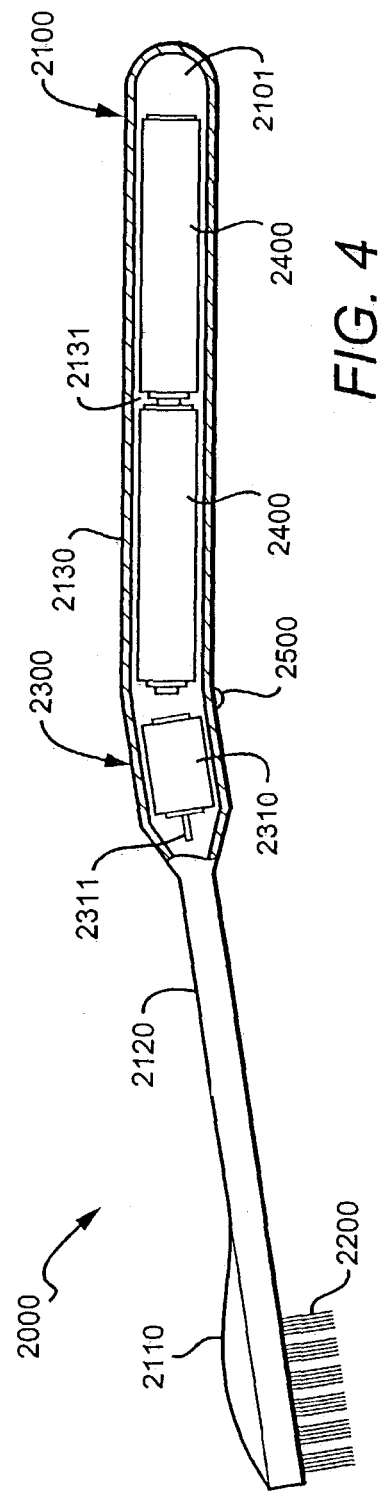

TOOTHBRUSH WITH TUNED VIBRATING HEAD

INCORPORATION BY REFERENCE

Applicant(s) hereby incorporate herein by reference, any and all U.S. patents, U.S. patent applications, and other documents and printed matter cited or referred to in this application.

BACKGROUND OF THE INVENTION

1. Field of the Invention

The field of the invention is hand held electric appliances and more particularly electric toothbrushes.

2. Description of Related Art

The benefits of electric toothbrushes are well known. One type of electric toothbrush utilizes an eccentrically moving weight coupling to motor's rotating shaft to cause a handle of the toothbrush to vibrate, the vibration of the handle being transmitted to the bristles of the brush via a neck coupling the bristle portion/head of the brush to the handle. The use of such devices is not always desirable however, at least in part because of the relatively large amount of vibration required in the handle in order to get an acceptable amount of vibration of the bristles, and the corresponding high energy usage and the uncomfortable degree of vibration transferred to the hand of a person using such a brush. Examples of such prior art toothbrushes can be found in U.S. Pat. Nos. 3,685,080, 5,421,726, 5,651,157, 5,706,542, 5,718,667, and 5,706,542. An eccentric weight, as the term is used herein, is a weight whose center of mass is not on the center of rotation of the weight.

Unfortunately, current toothbrushes are constructed in a manner that is cost prohibitive. Moreover, such toothbrushes are unduly cumbersome because of their weight, and size, and/or because of a battery charger accessory. Thus, there is a continuing need for affordable electric toothbrushes that are not unduly cumbersome, are relatively inexpensive and do not use excessive energy.

The following art defines the present state of this field:

Giuliani et al., U.S. Pat. No. 5,189,751 describes a vibrating toothbrush, which includes a toothbrush body and a lever arm having toothbrush bristles at one end thereof. The lever arm is mounted for pivotal movement at a pivot member, which is in the vicinity of the other end of the lever arm. In one embodiment, a pair of permanent magnets are provided at the other end of the lever arm, positioned side-by-side with opposite polarities. An electromagnet is provided to the rear of the lever arm. The electromagnet includes an E-core having top, bottom and center legs with a coil wound around its center leg which receives an alternating current driving signal from an oscillator/battery section. The frequency of operation is in the range of 150-400 Hz. The action of the alternating current in the electromagnet causes the lever arm to move about the pivot member, first in one direction and then in an opposing direction to provide the desired vibrating effect.

Hahn, et al., U.S. Pat. No. 5,987,681 describes an electric toothbrush with a handle, a brush head and a shank, which connects the handle to the brush head. A rotary motor is arranged in the handle and drives an unbalanced mass. The unbalanced mass driven by the motor is supported on one side or on both sides in the shank close to the brush head and is driven via an extended drive shaft, preferably an intermediate shaft, by the motor.

McDougall, U.S. Pat. No. 6,421,866 describes an electric toothbrush having a balanced mass provided on a shaft extension that rotates freely about a longitudinal axis, inside a cavity in a brush head. The shaft extension and the brush head are flexibly coupled to a drive shaft and to a remote end of a shank respectively. When the shaft is rotated by an electric motor in a handle, of the toothbrush, an offset stub axle, effectively at a remote end of the shaft extension and fitted to a bearing in the brush head, causes the brush head to vibrate. The shank is not caused to vibrate to any extent.

Wolf, Susan, Hendrix, Ph.D., Suzanne (1998). *Automated Toothbrush Comparison Statistical Report*. Clinical Research Associates, describes an evaluation of 6 toothbrushes that was performed using two populations to determine if toothbrushes with sonic or ultrasonic capabilities reduce dental plaque, more effectively than a manual or other automated toothbrushes. The Sensonic (Teledyne) and Sonicare (Optiva) toothbrushes claim sonic capabilities and the Ultrasonex (Sonex) claims ultrasonic capabilities. Control toothbrushes were the Interplak (Corsair) and Ultra Plaque Remover (Braun), which are automated toothbrushes not claiming sonic or ultrasonic capabilities, and the Advantage (Oral-B) manual toothbrush. Population one consisted of 24 non-handicapped subjects, while Population two consisted of 24 institutionalized handicapped subjects. Non-handicapped subjects were included to represent the majority of the population, while handicapped subjects were included because they have been reported as having frequent problems with heavy plaque in their oral cavities due to lack of manual dexterity necessary for effective tooth brushing.

Staff. (1998, July). CRA Status Report: Toothbrushes, Sonic & Ultrasonic. *CRA Newsletter*. P. 2-3, provides a comparison between sonic, ultrasonic, and manual toothbrushes. CRA laboratory & clinical studies compared plaque removal capability, test subject preferences, durability, & maintenance of 6 different toothbrushes over a 1¼ year period.

The prior art teaches vibrating toothbrushes, rotary bristle toothbrushes, and laterally oscillating toothbrushes. The prior art also includes electric toothbrushes in common use such as the Advantage by Oral-B, Interplak by Conair, Sensoic by Teledyne, Sonicare by Optiva, Ultra PR by Braun and Ultrasonex by Sonex. However, the prior art does not teach the matching of the natural frequency of vibration of the toothbrush itself with the purposely generated vibration frequency of the operational engine of the toothbrush. The present invention fulfills these needs so as to enable low energy usage, low energy loss in the handle of the device, improved vibratory action in the bristles and other benefits, and provides further related advantages as described in the following summary.

SUMMARY OF THE INVENTION

The present invention teaches certain benefits in construction and use which give rise to the objectives described below.

The present invention is directed to a toothbrush that utilizes a rotating eccentric weight positioned in or near the head of the toothbrush to cause movement of the head relative to a handle of the toothbrush, and methods relating to same. Positioning the weight in or near the head produces a toothbrush having numerous advantages over manual toothbrushes as well as powered toothbrushes. Such advantages include (a) use of a relatively low power motor; (b) lighter appliance weight; (c) reduced handle vibration; (d) longer battery life; (e) higher reliability; and/or (f) disposability. The phrase "near the head" is used herein to indicate that the weight is at least closer to the head than to the body/handle.

Disposable embodiments are possible as the use of a low power motor permits the toothbrush to operate for longer periods without recharging its batteries. This may result in having a single battery or set of batteries last as long as the bristles of the brush. The use of a lower power motor, a simple movement mechanism, non-rechargeable batteries, and non-replaceable bristles permits the total cost of the brush to be brought to a level where it is reasonable to dispose of the toothbrush after the bristles wear out and/or batteries are drained. Making the toothbrush disposable permits the batteries to be permanently sealed inside the toothbrush which in turn increases safety while reducing manufacturing costs.

A primary objective of the present invention is to provide an apparatus and method of use of such apparatus that provides advantages not taught by the prior art.

Another objective is to provide such an invention capable of maximizing the amount of vibration energy delivered to the head.

A further objective is to provide such an invention capable of improved operation with long battery life.

A still further objective is to provide such an invention capable of inexpensive production.

A still further objective is to provide such an invention capable of replacement of a brush head.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the present invention. In such drawings:

FIG. 1 is a longitudinal sectional view of a first toothbrush embodying the invention;

FIG. 2 is a series of schematic representations of the motion of a weight positioned on a shaft within the head of the toothbrush of FIG. 1 as viewed from one end of the shaft;

FIG. 3A is a schematic representation of the motion of the head of the toothbrush of FIG. 1 for embodiments where the motion is circular/orbital;

FIG. 3B is a schematic representation of the motion of the head of the toothbrush of FIG. 1 for embodiments where the motion is in the direction of the bristles of a brush of the invention;

FIG. 3C is a schematic representation of the motion of the head of the toothbrush of FIG. 1 for embodiments where the motion is lateral to the direction of the bristles of the brush of the invention;

FIG. 4 is a partial sectional view of a second toothbrush embodying the invention;

DETAILED DESCRIPTION OF THE INVENTION

Figure 5A:
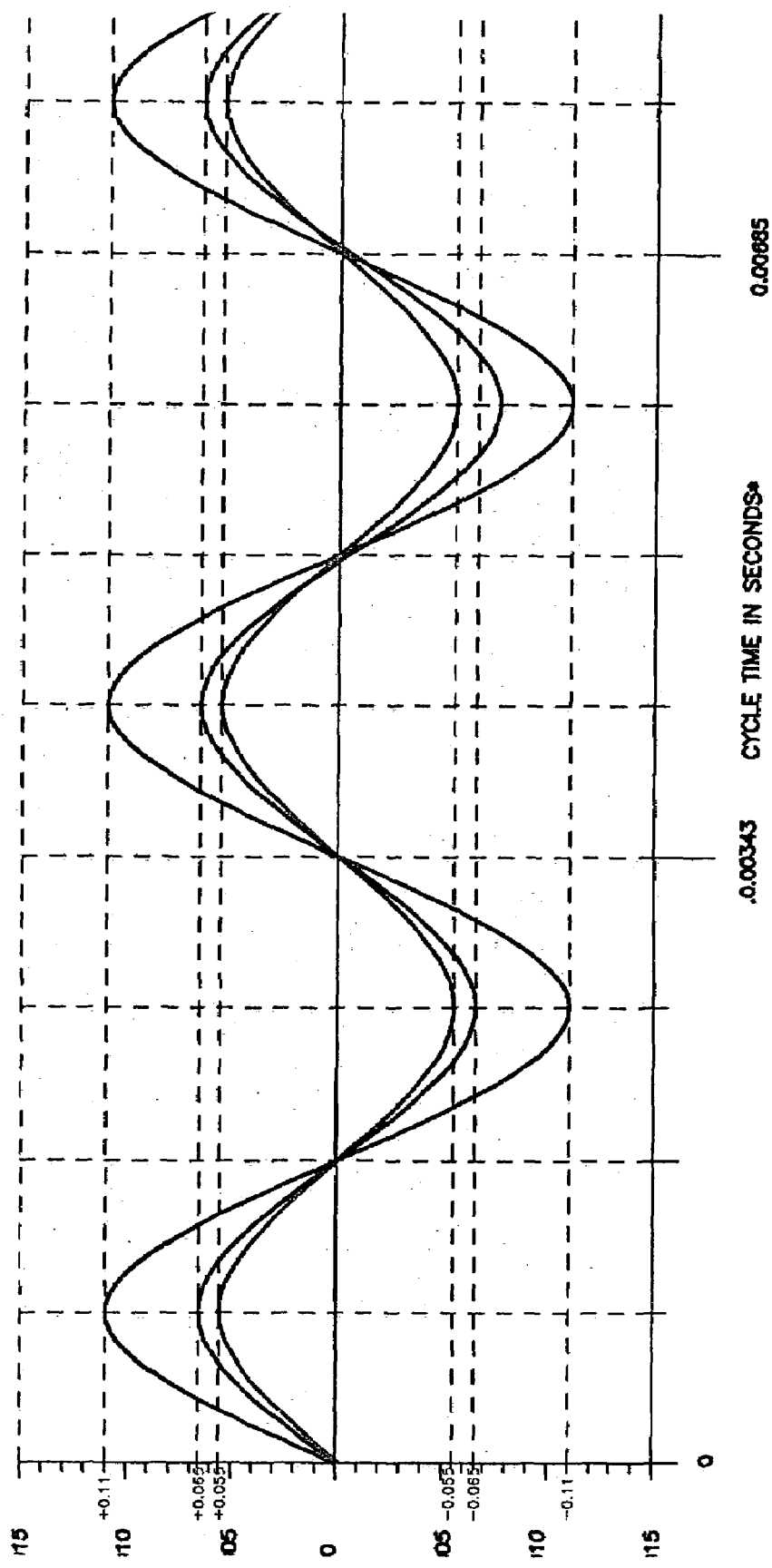
FIG. 5A is a graph showing the effects of tuning on toothbrush head vibration amplitude.

The above described drawing figures illustrate the invention in at least one of its preferred embodiments, which is further defined in detail in the following description. Referring first to FIG. 1, toothbrush 1000 comprises body 1100, bristles 1200, motion assembly 1300, power source(s) 1400, and control assembly 1500. Body 1100 comprises head 1110, neck 1120, and handle 1130. Head 1110 is that portion of body 1100 to which bristles 1200 are mounted. Neck 1120 is that portion of body 1100 that couples head 1110 to handle 1130. Handle 1130 is that portion of body 1100 that is adapted to be gripped by a hand of a persen using toothbrush 1000. Body 1100 also comprises body cavity 1101 that is subdivided into cavities corresponding to head 1110, neck 1120, and handle 1130. The sub-cavities of body cavity 1101 are head cavity 1111, neck cavity 1121, and handle cavity 1131. Motion assembly 1300 comprises motor 1310, motor spindle 1311, coupler 1312, flexible wire shaft 1320, shaft bearing 1321, weight 1330, and weight well 1331. Power source 1400 comprises two AAA batteries. Control assembly 1500 comprises the switches and circuitry used to control the movement of weight 1330 by controlling the use of motor 1310.

Distance D1 is the distance from the tip of toothbrush 1000 to the center of mass of weight 1330. Distance D2 is the distance from the center of mass of weight 1330 to motor 1310. Distance D3 is the total length of the head 1110 and neck 1120 portions of body 1100. Distance D4 is the length of handle 1130.

Body 1100 is preferably formed as a plurality of molded plastic pieces, the pieces coupled together in a manner which hermetically seals the body cavity 1101. Sealing the various components of motion assembly 1300 and power assembly 1400 within body cavity 1101 is contemplated to increase the life of motion assembly 1300 and power assembly 1400 by preventing dirt, water, or other substances from affecting these parts and also prevents any chemicals or parts from the components adversely affecting a user of toothbrush 1000.

Head 1110 and handle 1130 preferably has a size and shape suitable for being used in a manner similar to common toothbrushes in use. The handle cavity 1131 is preferably sized and dimensioned to securely hold power source 1400. Head cavity 1111 is preferably sized and shaped to position and permit proper operation of the weight 1330 and shaft 1320, and to properly position the weight well 1331 and shaft bearing 1321 of motion assembly 1300.

Neck 1120 is preferably sized and dimensioned to provide a desired overall length and flexibility and to contain neck cavity 1121. Neck cavity 1121 is preferably sized and dimensioned to allow flexible wire shaft 1320 to extend from the motor 1310 to the shaft bearing 1321 without having flexible wire shaft 1320 contact the sidewalls of neck cavity 1121. It is contemplated that the structure of neck 1120 may vary between embodiments, with the variance in structure resulting in different motions for head 1110 as weight 1330 rotates.

Looking at FIGS. 3A-3C, it is known that structural shape, material type, and wall thickness variations of neck 1120 will result in motions of head 1110 that may be in the direction of the bristles 1200, iateral to the bristles 1200, circular, or some combination of these motions. In FIG. 3A, the motion M1 of head 1110 is circular/orbital in that head 1110 moves along a path that is at least somewhat similar to the circle shown having a radius M1R, where movement distance M1V is approximately equal to movement distance M1H. In FIG. 3B, the motion M2 of head 1110 is in line with bristles 1200 in that movement distance M2V is substantially larger than the horizontal movement distance M2H. In FIG. 3C, the motion M3 of head 1110 is horizontal in that horizontal movement distance M3H is substantially larger than the vertical movement distance M3V.

Bristles 1200 are preferably permanently mounted to head 1110. It an alternate embodiment, however, the bristles 1200 may be removeably mounted to head 1110 for ease of replacement. Similarly, head 1110 and neck 1120 may be removeably coupled to each other and/or neck 1120 may be removeably coupled to body 1130.

Motion assembly 1300 is used to convert energy from power source(s) 1400 to movement of head 1110. In the preferred embodiment, the motor spindle 1311 is coupled to flexible wire shaft 1320 by a coupling 1312 such as a flexible tube, or universal joint or other joint capable of isolating the head 1110 and the motor 1310 so that when power is applied to motor 1310, spindle 1311 and flexible wire shaft 1320 rotate together. Weight 1330 is mounted to flexible wire shaft 1320 such that flexible wire shaft 1320 does not pass through the center of gravity of weight 1330 as can be clearly seen in FIGS. 1 and 2. FIG. 2 illustrates the motion of weight 1330 as flexible wire shaft 1320 rotates to cause the head to move as illustrated in FIGS. 3A-3C. Because weight 1330 is off center with respect to tis rotation, it wobbles generating lateral thrusts. Weight well 1331 permits weight 1330 to rotate without contacting any of the side walls of head cavity 1111. The lateral thrusts of weight 1330 are transferred to head 1110 via shaft bearing 1321. Shaft bearing 1321 is preferably chosen to minimize the noise generated by the rotation of flexible wire shaft 1320 and weight 1330. In summary, while fixed to shaft 1320, weight 1330 is rotatably mounted within toothbrush 1000 as shaft 1320 is caused to rotate within the toothbrush 1000.

For improved motion of head 1110, distance D1 is less than distance D2. Preferably, distance D2 is at least 50 mm or 2 inches. Similarly, distance D1 is preferably less than 12.5 mm or 0.5 inches. Preferably, the ratio of D2 to D1 is at least 4:1. Preferably, the distance between weight 1330 and shaft bearing 1321 is minimal to maximize the transfer of motion of weight 1330 to head 1110. Shaft bearing 1321 may also be positioned between weight 1330 and motor 1310 in an alternate embodiment.

Preferably, shaft 1320 and coupling 1312 are flexible so as to isolate the lateral thrusts of the weight 1330 from the handle 1100, motor 1310 and power source 1400. The amount of flexibility in shaft 1320 and coupling 1312 may vary, although it is preferred that as shaft 1320 is made stiffer, coupling 1312 is made more flexible and vice-versa.

Power source 1400 is preferably battery cells such as AAA size batteries. However, alternative embodiments may use different types of batteries or capacitors as power source 1400. It is preferred that the choice of power source be made such that the amount of time that power source 1400 is able to adequately power motor 1310 is at least 8 hours, and preferably at least 9-12 hours. If usage is about 2 minutes per day, the operational life of the toothbrush is approximately 8 months for an 8 hour battery life, and 9-12 month for a 9-12 hour life.

Control assembly 1500 may comprise a simple switch used to complete or break an electrical connection (not shown) between power source 1400 and motor 1310. Such connections are well known in hand held flashlights. However, alternative embodiments may use more complex means of motor control.

FIG. 4 illustrates an alternate embodiment having an angled neck. As shown in FIG. 4, toothbrush 2000 comprises body 2100, bristles 2200, motion assembly 2300, power source(s) 2400, and control assembly 2500. Body 2100 comprises head 2110, neck 2120, and handle 2130. Head 2110 is the portion of body 2100 to which bristles 2200 are mounted. Neck 2120 is the portion of body 2100 that couples head 2110 to handle 2130. Handle 2130 is the portion of body 2100 that is adapted to be gripped by the hand of a person using toothbrush 2000. Body 2100 also comprises body cavity 2101 that is subdivided into cavities corresponding to head 2110, neck 2120, and handle 2130. The only sub-cavity of body cavity 2101 shown is handle cavity 2131. Motion assembly 2300 comprises motor 2310 and motor spindle 2311, as well as a coupler, flexible wire shaft, shaft bearing, weight, and weight well which are similar to those shown in FIG. 1. Power source 2400 comprises two AAA batteries. Control assembly 2500 comprises the switches and circuitry used to control the use of motor 2310.

The use of either toothbrush 1000 or 2000 can be described as using an electric toothbrush having an eccentric weight located within a head of the toothbrush to rotate and, while the weight is rotating, using the toothbrush to brush teeth. More specifically, causing an eccentric weight to rotate comprises electrically connecting an electric motor to a power source so as to cause a motor spindle to rotate, the motor spindle causing a shaft to rotate, the shaft causing the eccentric weight to rotate and transfer its lateral thrusts to the head 2110 of the toothbrush 2000 thereby causing brushing action against teeth and gums.

In the present invention rotational energy imparted to the off center mounted weight 1330 is converted to side thrusting forces, i.e., away from the longitudinal axis of the head 1110 and neck 1120, which causes the head 1110 and bristles 1200 to move laterally as previously described. Important parameters that are associated with the type and magnitude of such lateral movements are the amount of the off center weight 1330, the speed of rotation of the shaft 1320, the flexibility of the shaft 1320 in conjunction with the separation distance between the weight 1330 and the bearing 1321 because this distance is proportional to the diameter of the circle swept by the weight 1330; these all being proportion to the magnitude of the side thrust forces created and thus the magnitude of head movement. Stiffness of the head 1110 and the neck 1120 is inversely proportional to head movement.

As stated, because the side thrust forces are generated in the head 1110, it is primarily the head 1110 that tends to be moved, which is desirable, however, the shaft 1320 and neck 1120 are flexible in order to provide vibrational isolation between the handle 1130 and the head 1110, some of the energy created by the spinning weight 1330 is necessarily transmitted to the handle 1130 and therefore lost relative to the total energy potentially available for head movement. This is clearly undesirable and is minimized by fashioning the neck 1120 and head 1110 in such a manner that its natural resonance frequency (primary harmonic) is nearly the same as the rotational frequency of the off center mounted weight 1330. When this is true the weight 1330 on each one-half rotation away from the bristles 1200 tends to flex the head 1110 away from the tooth surface (not shown), and when, on the next one-half rotation when the weight 1330 moves toward the bristles 1200 it tends to pull the head 1110 toward the tooth surface and this movement of the head 1110 is augmented by the natural flexing of the head 1110 toward the tooth surface due to the elastic restoring action of the material of the head 1110 and neck 1120. The natural flextural movement of the head 1110 and neck 1320 are synchronized with the movement of the weight 1330.

Figure 5B:
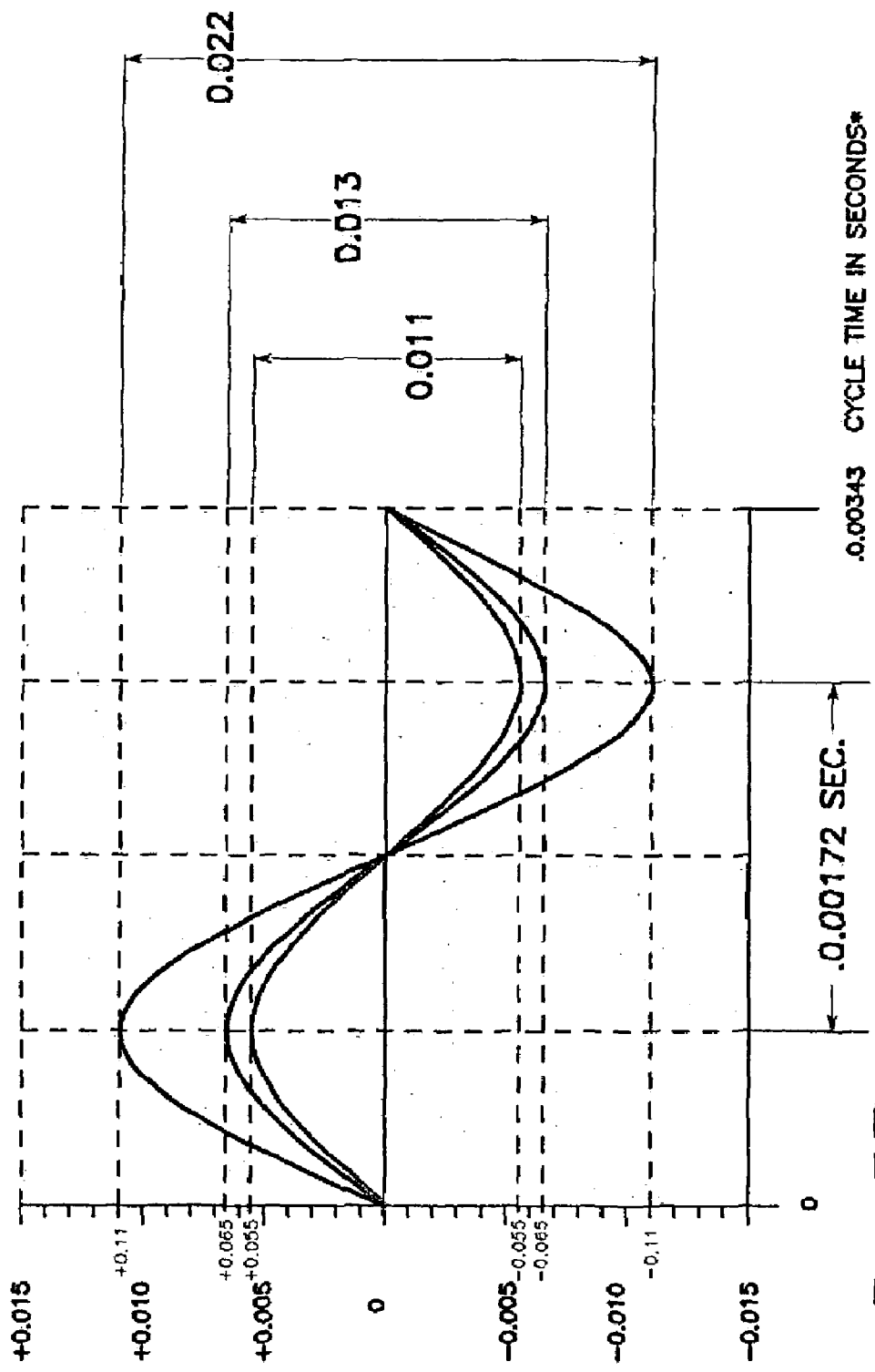
FIG. 5B is a graph showing the effects of tuning on toothbrush head velocity.
Figure 6:
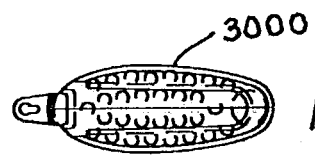
FIG. 6 is a plan view of a removable brush of the invention.
Figure 7:
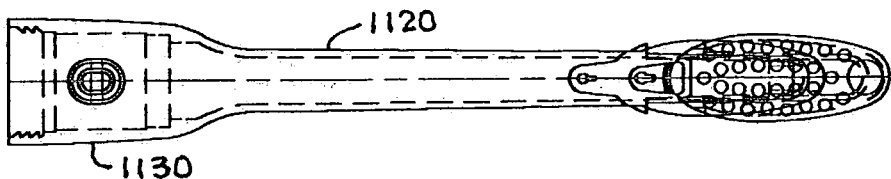
FIG. 7 is a plan view of a neck and head of the invention with the removable brush shown partially and also fully installed on the head.
Figure 8:
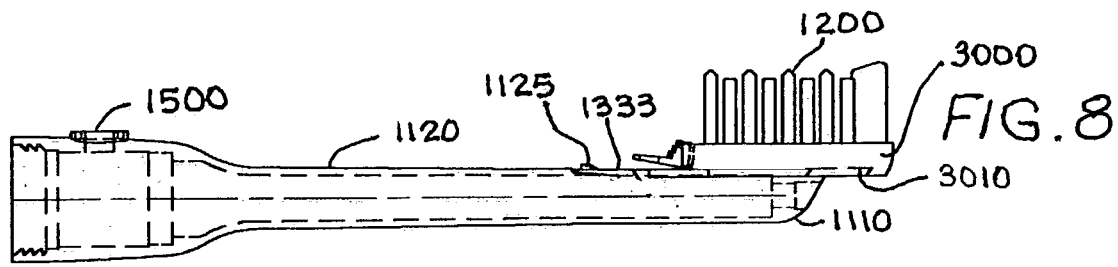
FIG. 8 is a side elevational view of the neck and head of the invention showing the removable brush in the partially installed position.
Figure 9:
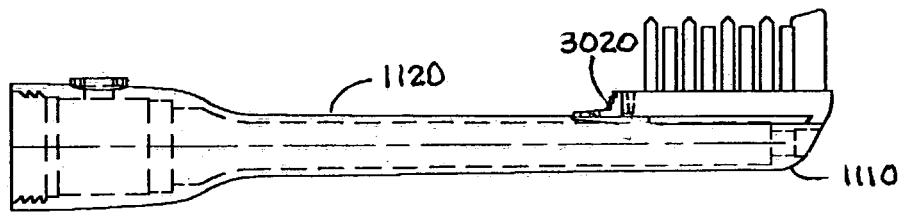
FIG. 9 is a side elevational view of the neck and head of the invention showing the removable brush in the fully installed position.

The result of tuning, as defined above, is shown in FIGS. 5A and 5B. FIG. 5A is a plot of the magnitude of head 1110 excursion on the y axis versus time plotted on the x axis. It should be noted that the cycle time is constant, i.e., 0.00343 seconds per revolution. This is the rotational speed of the motor used; 17,500 rpm. However, as shown, the magnitude of the excursion of the head 1110 varies with its tuned reflex frequency. The greatest excursions were obtained when the neck and head were tuned to 17,500 cycles per minute (cpm). Smaller excursions were obtained with neck and head tuned to 10,000 cpm and 8,000 cpm respectively. As stated above, the head and neck are tuned by adjustment of the neck length, material stiffness, wall thickness and other physical parameters. As shown in FIG. 5B the velocity of the head of the synchronously tuned neck and head is significantly greater than the mistuned units. It may be shown that the synchronously tuned unit develops at least four-times the cleaning energy then does the least well tuned unit.

FIGS. 6-9 teach a preferred embodiment of the invention wherein a removable brush 3000 is attached to the head 1110 via a sliding engagement. The removable brush 3000 has a first engagement element 3010, preferably a slot on its underside, while head 1110 has a second engagement element 1333, preferably a finger conforming to the slot, so that the elements 1333 and 3010 are preferably interlocking as is known in the art when the brush 3000 is slid onto the head 1110. A tab 3020 of the brush 3000 is positioned for engaging a tab receiver 1125 on the neck 1120 for holding the brush 3000 in place. When worn out, the brush 3000 may be removed and replaced with a substitute of the same design by merely snapping the tab 3020 away from the tab receiver 1125 and sliding the worn brush 3000 off the head 1110, and then installing a new brush 3000 by reversing the process of removal.

Figure 10:
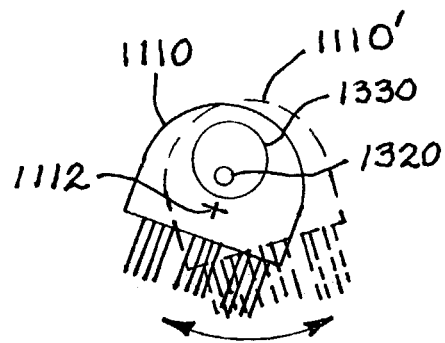
FIG. 10 is a schematic diagram showing an end view of the head in two extreme positions of its vibration.

FIG. 10 shows graphically the preferred embodiment of the invention where the center of mass 1112 of the head 1110 is laterally offset from the drive shaft 1320. In this case, the head 1110 is caused to flex about its longitudinal axis transferring elastic spring energy as it oscillates from side to side in synchronization with the rotating weight 1330, as shown in the figure with the head 1110 shown in solid line in the extreme left side oscillation position, and numeral 1110' shown in broken line in the extreme right side oscillation position.

While the invention has been described with reference to at least one preferred embodiment, it is to be clearly understood by those skilled in the art that the invention is not limited thereto. Rather, the scope of the invention is to be interpreted only in conjunction with the appended claims and it is made clear, here, that the inventor(s) believe that the claimed subject matter is the invention.

What is claimed is:

1. An electrically powered toothbrush apparatus comprising: a removable and replaceable brush with bristles slidably attached via sliding engagement means to a head, a hollow neck portion supporting the head and extending from the head to handle, the neck portion being engaged with, and removably secured, to abut and directly contact the handle;

a self-supporting, elongate, one piece, flexible wire shaft connected a motor at one end and extending to a remote end of the toothbrush within the head, the motor being disposed within the handle and connected to the wire shaft by a drive shaft and flexible coupling; a weight eccentrically mounted on the wire shaft within the head and adjacent the bush to effect rotational and lateral motion therewith at a resonant sonic frequency, the wire shaft being isolated from the neck portion; the remote end of the drive shaft terminating in an anchored bearing in the head adjacent the weight; wherein the shaft is unsupported, free from contact, between its ends, whereby, the head, and neck portion are provided a resonant frequency of vibration approximately matched to the rotational speed of the weight.

2. The apparatus of claim 1 wherein the sliding engagement means comprises a first and second mutually joinable engagement elements.

3. The apparatus of claim 1 wherein the removable brush provides a tab.

4. The apparatus of claim 3 wherein the neck portion provides a tab receiver engageable with the tab of the removable brush for securement of the removable brush on the head.

5. The apparatus of claim 1, wherein a center of mass of the head is laterally offset from the drive shaft and wherein the neck portion and head are flexible so as to oscillate in synchronized rotational motion about a longitudinal axis of the drive shaft as the weight rotates.

6. The toothbrush apparatus of claim 1, in which the resonant frequency is -17,500 cpm.

7. The toothbrush apparatus of claim 1, in which the resonant frequency is -10,000 cpm.

8. The toothbrush apparatus of claim 1, in which the resonant frequency is 8,000 cpm -.

9. The toothbrush apparatus of claim 1, in which an electrical power source comprised of at least one sealed battery is provided in said handle.

* * * * *